US009155517B2

(12) United States Patent
Dunbar et al.

(10) Patent No.: US 9,155,517 B2
(45) Date of Patent: Oct. 13, 2015

(54) OPTO-ELECTRICAL ULTRASOUND SENSOR AND SYSTEM

(75) Inventors: Allan Dunbar, Jena (DE); Eliseo Sobrino, Jena (DE); Sicco Schets, Jena (DE); Uwe Zeitner, Weimar (DE)

(73) Assignee: EZONO AG, Jena (DE)

( * ) Notice: Subject to any disclaimer, the term of this patent is extended or adjusted under 35 U.S.C. 154(b) by 351 days.

(21) Appl. No.: 12/669,015

(22) PCT Filed: Jul. 1, 2008

(86) PCT No.: PCT/EP2008/058465
§ 371 (c)(1),
(2), (4) Date: Feb. 23, 2010

(87) PCT Pub. No.: WO2009/010386
PCT Pub. Date: Jan. 22, 2009

(65) Prior Publication Data
US 2010/0210950 A1      Aug. 19, 2010

(30) Foreign Application Priority Data
Jul. 13, 2007   (EP) .................................... 07112399

(51) Int. Cl.
*A61B 8/14* (2006.01)
*A61B 8/00* (2006.01)
(Continued)

(52) U.S. Cl.
CPC ................ *A61B 8/00* (2013.01); *A61B 5/0097* (2013.01); *G01H 9/00* (2013.01); *G01S 7/52033* (2013.01); *G01S 7/52079* (2013.01); *G01S 15/8968* (2013.01); *A61B 5/0066* (2013.01)

(58) Field of Classification Search
CPC ............................. G01N 2201/067; G01B 9/02
USPC ........................... 600/459, 407, 437; 356/339
See application file for complete search history.

(56) References Cited

U.S. PATENT DOCUMENTS

| 2,612,074 A | 9/1952 | Mirau et al. |
| 4,381,676 A | 5/1983 | Kaule et al. |
| (Continued) | | |

FOREIGN PATENT DOCUMENTS

| EP | 1156345 | 11/2001 |
| EP | 1559373 A1 | 8/2005 |
| WO | WO/03/100363 | 12/2003 |

OTHER PUBLICATIONS

International Search Report and Written Opinion for PCT/EP2008/058465, mailed Aug. 29, 2008.
(Continued)

*Primary Examiner* — Joel F Brutus
(74) *Attorney, Agent, or Firm* — Birch, Stewart, Kolasch & Birch, LLP

(57) ABSTRACT

An opto-electrical ultrasound sensor, preferably for the use in medical diagnostics, comprising at least one light source (2), a photo detector (3) illuminated by the light source (2) and capable of producing an electrical signal indicative of the intensity of the light incident on the photo detector (3), and an optical ultrasound detector (4) located in the optical path between the light source (2) and the photo detector (3) and capable of modulating in response to an ultrasound signal the intensity of at least part of the light incident on photo detector (3) from the light source (2). The opto-electrical ultrasound sensor further comprises intensity adjustment means (5) for adjusting the intensity of the light incident on the photo detector (3) via the optical ultrasound detector (4).

19 Claims, 3 Drawing Sheets

(51) Int. Cl.
*G01H 9/00* (2006.01)
*G01S 7/52* (2006.01)
*G01S 15/89* (2006.01)
*A61B 5/00* (2006.01)

(56) References Cited

U.S. PATENT DOCUMENTS

| | | | |
|---|---|---|---|
| 4,762,413 A * | 8/1988 | Namba et al. | 356/339 |
| 5,146,079 A * | 9/1992 | Lisco | 250/214 AG |
| 5,153,667 A * | 10/1992 | Aoshima et al. | 356/218 |
| 5,735,276 A * | 4/1998 | Lemelson | 600/407 |
| 5,791,907 A | 8/1998 | Ramshaw et al. | |
| 5,832,055 A * | 11/1998 | Dewaele | 378/62 |
| 6,390,978 B1 | 5/2002 | Irion et al. | |
| 6,488,629 B1 | 12/2002 | Saetre et al. | |
| 7,041,058 B2 | 5/2006 | Piehler | |
| 7,263,710 B1 | 8/2007 | Hummel, Jr. | |
| 2001/0010003 A1 * | 7/2001 | Lai | 606/107 |
| 2001/0039836 A1 * | 11/2001 | Ogawa | 73/608 |
| 2001/0042410 A1 * | 11/2001 | Ogawa | 73/656 |
| 2002/0087080 A1 | 7/2002 | Slayton et al. | |
| 2004/0019270 A1 | 1/2004 | Takeuchi | |
| 2005/0068221 A1 * | 3/2005 | Freeman et al. | 341/161 |
| 2005/0096545 A1 * | 5/2005 | Haider et al. | 600/447 |
| 2007/0239001 A1 * | 10/2007 | Mehi et al. | 600/437 |
| 2008/0249402 A1 | 10/2008 | Szucs et al. | |

OTHER PUBLICATIONS

International Search Report and Written Opinion for patent application PCT/EP2008/054832, mailed Oct. 2, 2006.

* cited by examiner

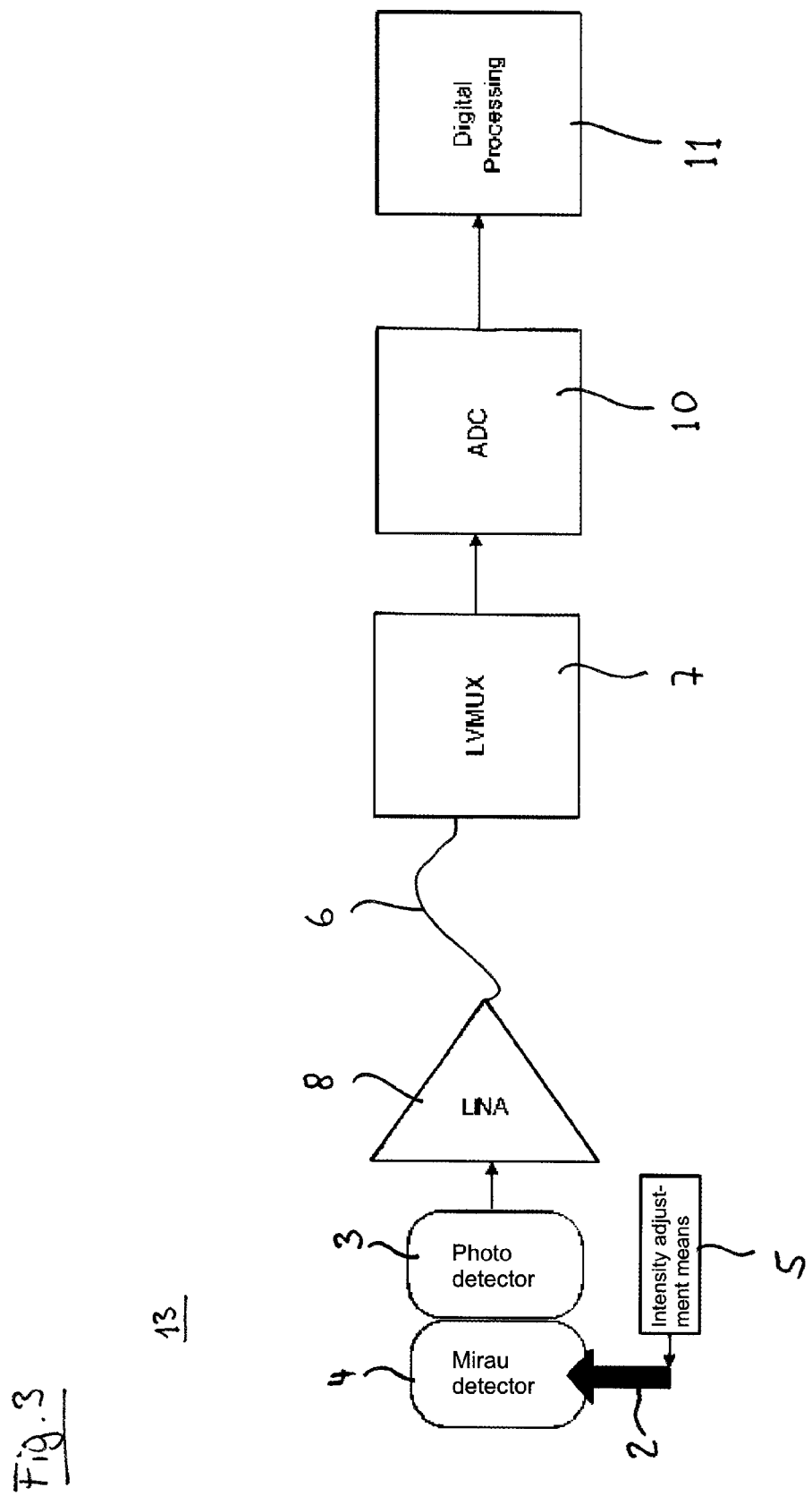

OPTO-ELECTRICAL ULTRASOUND SENSOR AND SYSTEM

BACKGROUND OF THE INVENTION

The invention relates to an opto-electrical ultrasound sensor, preferably for the use in medical diagnostics, according to the pre-characterizing clause of claim 1. It further relates to an ultrasound system according to the pre-characterizing clause of claim 9. Finally, the invention relates to a method of detecting ultrasounds according to the pre-characterizing clause of claim 21.

STATE OF THE ART

A medical diagnostic ultrasound system typically comprises a hand-held probe that includes an array of ultrasound transducers which both transmit ultrasound energy into a region to be examined and receive reflected ultrasound energy returning from that region. To generate ultrasound pulses, a driver circuit of a processing unit sends precisely timed electrical signals to the transducers. Part of the ultrasound pulses is reflected in the region to be examined and returns to the transducers. The transducers then convert the received ultrasound energy into low-level electrical signals which are transferred to the processing unit of the system. The processing unit amplifies and combines the signals from the transducers to generate an image of the examined region.

A bundle of cables, though which the electrical signals are passed, usually connects the hand-held probe with the processing unit. To avoid electrical cross-talk and other electrical interference, coaxial cables are used. State-of-the-art medical ultrasound systems use arrays of about 100 separate ultrasound transducers each of which is connected with the processing unit via a separate coaxial cable. There is a general trend towards greater numbers of transducers at from line arrays to two-dimensional arrays in order to increase the image quality of the system.

Conventional transducers exploit the piezo-electric effect to convert electrical energy into ultrasound and vice versa. Typical transducer materials are PZT and PVDF. The fact that the same piezo-electric transducers are used for both ultrasound generation and detection complicates signal processing in the processing unit. This is in particular because transmit/receive switches must switch the transducers precisely and uniformly between transmission and reception modes. Moreover, the returned signals can be up to 100 dB smaller than the transmitted signals, entailing demanding requirements as to the dynamic range of the processing electronics. In particular, recovery after a large transmission signal must be fast and on/off (extinction) ratios must be high.

Apart from piezo-electric methods optical methods of ultrasound detection are also known in the art, even though generally they are only used in non-medical applications, in particular for Non-Destructive Testing (NDT). The advantage of optical methods over conventional piezo-electric sensor becomes apparent when considering small ultrasound arrays on a micrometer scale. As the size of a piezo-electric transducer element is reduced, detection noise increases considerably. By contrast, the effective area of an optical ultrasound sensor, which is determined by the size of the confined optical field, can be scaled down to micrometer size without a substantial increase in detection noise.

Optical ultrasound sensors function by detecting the light reflected from a surface which is excited by the ultrasound to vibrate, typically with amplitudes in the range of one tenth of a nanometer to a few nanometers. These vibrations produce a small phase shift or frequency shift according to the Doppler effect in the scattered light, which is detected by an interferometer. Essentially, two approaches for detection are employed in the art: (1) reference beam interferometry (also called optical heterodyning) and (2) time-delay interferometry (also called velocity interferometry). In reference beam interferometry, a surface which is excited by the ultrasound to vibrate, acts as a mirror of the interferometer. The wave reflected from the surface interferes with a reference wave in the interferometer. In time-delay interferometry, on the other hand, light reflected from the surface is frequency or phase demodulated by an interferometer which creates a time delay between interfering waves. In this case, the surface is not part of the interferometer. A Michelson, a Mach-Zehnder, or a Fabry-Perot interferometer can be used, for example.

The co-pending German patent application DE 10 2006 033 229 describes an ultrasound sensor based on a variation of a Mirau interferometer as for example disclosed in U.S. Pat. No. 2,612,074 and in more detail in "Surface profiling by frequency-domain analysis of white-light interferograms", Peter de Groot and Leslie Deck, Proc. SPIE 2248, pp. 101-104, 1994, and "High-speed noncontact profiler based on scanning white-light interferometry", Leslie Deck and Peter de Groot, Applied Optics, vol. 33, no. 31, 1994. A Mirau interferometer that inspects an ultrasound-excited membrane is located in the optical path from a light source, e.g. a laser, to a photo detector, e.g. a photo diode. In a preferred embodiment, an array of Mirau interferometers and an array of photo detectors are provided, each interferometer being associated with one corresponding photo detector. The detectors are coupled with an analysis and/or imaging processing unit.

Problem to be Solved by the Invention

It is an objective of the present invention to provide an improved opto-electric ultrasound sensor, e.g. for the use in medical diagnostics. The invention further aims to provide an improved ultrasound system and an improved method of detecting ultrasound, in particular for the use in medical diagnostics.

Solution According to the Invention

According to the invention, the problem is solved by providing an opto-electrical ultrasound sensor according to claim 1, an ultrasound system according to claim 9 and a method of detecting ultrasound according to claim 21.

Due to the intensity adjustment means of the opto-electrical ultrasound sensor according to the invention the performance of the device can be improved, e.g. by adjusting the intensity to the dynamic range of the photo detector or the components upstream from there. The intensity adjustment means may also perform tasks or parts of tasks otherwise performed by special components of the processing unit such as Time Gain Control (TGC) or saturation protection, thereby reducing the complexity of such components or rendering them redundant altogether.

The sensor, system, and method according to the invention may be used in medical diagnostics, e.g. in the areas of external obstetrics, gynaecology, paediatrics and cardiology. It may also be applied for internal examinations such as medical endocavity examinations, where an ultrasound probe is inserted into a natural orifice of a patient. Moreover, Non-Destructive Testing (NDT) is a promising area of application for the invention.

DESCRIPTION OF PREFERRED EMBODIMENTS OF THE INVENTION

Preferred features of the invention, which may be applied alone or in combination, are disclosed in the dependent claims.

In a preferred embodiment of the invention, the intensity adjustment means control the light source in order to adjust the intensity of the light emitted by the light source. In particular for light sources, the intensity of which can easily be controlled, e.g. by adjusting a supply voltage or current, this is a simple and straight forward method of adjusting the intensity of the light incident on the photo detector. Alternatively, the intensity adjustment means may comprise an attenuation means located in the optical path from the light source to the photo detector via the optical ultrasound detector to attenuate the light. The attenuation means may e.g. be an aperture or a liquid crystal device or an electro-optical device such as a Pockels cell or even an integrated optical device such as an electro-optical modulator. Achievable advantages of using a Pockels cell over a light source current or voltage control or an LCD are its extreme accuracy in control of light output and its speed of doing so. Preferably, the attenuation means is applied to control the splitting ratio of the two interfering beams in the interferometer. Preferably, the intensity adjustment means adjusts the light intensity according to an intensity control parameter, which may e.g. be a measure of the intensity of the light source or the degree of attenuation provided by the attenuation means.

The intensity adjustment, preferably the intensity control parameter, may vary as a function of one or several other parameters. In one preferred embodiment of the invention, it varies in a pre-determined way, e.g. as a function of time. In another preferred embodiment of the invention, it varies in response to the intensity of the light as registered by the photo detector. To compensate for attenuation of the ultrasound signal as it comes from greater depths in the tissue, it is known in the art to employ a Time Gain Control-mechanism (TGC, sometimes also called Depth Gain Control—DGC). TGC exploits the fact that due to the finite velocity of propagation of ultrasound waves, ultrasound signals that are reflected close to the surface where the ultrasound detector is located will reach the detector earlier than signals reflected deeper in the tissue. Further, the latter signals will experience greater attenuation. Thus, attenuation can be compensated for by amplifying the detected signals in a way that the amplification factor increases with time. Conventionally, this is achieved with a Variable Gain Amplifier (VGA) that is located downstream the ultrasound detector. Because the ultrasound signal is attenuated logarithmically as it propagates in the tissue, the VGA is linear in dB in order to essentially invert this function.

In a preferred embodiment, the intensity adjustment means adjust the intensity as a function of time, preferably periodically. Preferably, the intensity is increased linear in dB, preferably from or shortly after the moment in which the respective ultrasound signal has been emitted from the ultrasound transducer. It is an achievable advantage of this embodiment of the invention that the intensity adjustment means can at least partially compensate for an attenuation of the ultrasound signal as it comes from greater depths in the object to be studied. It is another achievable advantage of this embodiment of the invention that a linearity of the amplification achieved by adjusting the light intensity is more accurate than that achievable with conventional, electronic amplifiers, the latter being prone to a non-linear response to frequency changes. By shifting the TGC this way at least partly into the optical domain, it is also achievable that advantageously a smaller dynamic range of the photo detector and/or electronics behind it may be sufficient as compared to the conventional systems. In one embodiment of the invention, the time-dependent intensity adjustment entirely replaces the VGA in an ultrasound system, thereby advantageously allowing for reductions in cost, size, and/or power consumption of the system. In another embodiment, the time gain control is only partly performed by the intensity adjustment means. This may e.g. reduce the dynamic range the VGA is required to cover.

In a preferred embodiment of the invention, the intensity adjustment means adjust the intensity in response to the electrical signals produced by the photo detector. Preferably, the intensity is adjusted to better match the photo detector's dynamic range and/or the dynamic range of the electronics that process the electrical signals produced by the photo detector. With this embodiment of the invention, the dynamic range of the photo detector and/or the processing electronics can be better exploited, thereby increasing image quality and/or reducing power consumption.

In a particularly preferred embodiment of the invention, the intensity adjustment means can reduce the intensity of the light incident on the photo detector to prevent the electrical signals produced by the photo detector to exceed a pre-determined level. It is an achievable advantage of this embodiment of the invention, that saturation or overflow of the reception electronics can be avoided. In a particularly preferred embodiment, the intensity is already reduced, when the signal is expected to exceed a pre-determined level. This way, the intensity adjustment means may at least partially replace protection circuitry that is conventionally employed to prevent saturation or overflow. This may not only provide for a reduction in cost, size and/or power consumption but may also contribute to an improvement of image quality, as noise produced by protection circuitry can be avoided.

A preferred photo detector is part of an array of several photo detectors, each photo detector preferably being associated with one reception channel. Similarly, the preferred optical ultrasound detector is part of an array of several optical ultrasound detectors, each ultrasound detector preferably being associated with one photo detector.

In a preferred ultrasound system according to the present invention, the transmission channels comprise ultrasound transducers to generate an ultrasound signal, the ultrasound transducers being different from the ultrasound sensor. Because the transducer is different from the sensor, the transmission and reception channels of the ultrasound system can essentially be separate, the transmission channels including the transducers and the reception channels including the ultrasound sensors. With this embodiment of the invention, several advantages can be achieved. For example, cables for transmission and reception may be separate thereby considerably reducing cross-talk. Moreover, the cables for transmission only need to deal with high voltages, not both high and low voltages, which means that potentially lower quality and cheaper cables can be used. It is another achievable advantage that the number of transducers for transmission can be different from, preferably smaller than the number of ultrasound detectors. Fewer transducers for transmission may provide for a reduction in the number of co-axial cables connecting the individual transducers in the hand-held probe with the processing unit and/or the elimination or at least a reduction in the number of high-voltage multiplexers, conventionally used to combine several transmission channels. A reduction in co-axial cables may considerably improve the maneuverability of the hand-held probe by an operator.

It is another achievable advantage of the separate ultrasound generating transducers and ultrasound sensors, that transmission and reception can take place at the same time. This can be particularly advantageous if the ultrasound system is operated in the CW Doppler-mode. Moreover, in general reception can start much earlier than in traditional systems. As a result, it is possible to image closer to the surface, which may e.g. be advantageous in applications in dermatology.

It is a further achievable advantage of this embodiment of the invention that a transmit/receive switch can be omitted to switch a transducer between reception and transmission modes. Moreover, protection circuitry that in conventional systems protects the sensitive electronics of the reception channels from the high-power pulses of the transmission channels can be omitted. Advantageously, if no protection circuit is required, power transfer during transmit can be more efficient, because typically the protection circuit on conventional architectures absorbs some power from the transmitted pulse. Also, leakage between transmission and reception channels can be avoided if transmission the channels are separate from the reception channels. This may be of particular advantage in the CW Doppler mode where, conventionally, a sine wave is continuously transmitted with one half of the transducer array while the other half of the array is used for reception. Such operation generally entails strong leakage from the transmission channels to the reception channels.

It is one achievable advantage of the separate ultrasound generating transducers and ultrasound sensors that it is no longer required to make a compromise between a transducer design most suitable for reception and one most suitable for transmission. In one preferred embodiment of the invention, the ultrasound transducer for generating the ultrasound signal comprises the polymer PVDF (polyvinylidenedifluoride) as a piezo-electric material. Unlike PZT, which is the preferred piezo-electric material in conventional systems, PVDF is a broad band-material. It is an achievable advantage of this embodiment of the invention, that the amount of damping materials, as it is required in PZT-systems, can be reduced or damping materials can even be entirely omitted.

In another preferred embodiment of the invention, cellular polypropylene, which has a D33-coefficient (an indication of the transmission efficiency) that is fifteen times higher than that of piezo-ceramic materials such as PZT, is used for the ultrasound generating transducers. It is also conceivable to use a pulse laser directed at the object to be investigated as an ultrasound generator.

If the ultrasound sensors are separate from the ultrasound generating transducer, it is achievable, that only lower-voltage signals are present on the reception side. Thus, in one preferred embodiment of the invention, the reception channel comprises a low-voltage multiplexer. Achievable advantages of a low-voltage multiplexer as compared to the high-voltage multiplexer used in conventional systems includes reduced costs, a smaller size, a reduced power consumption and a lower resistance, which implies lower thermal noise and lower attenuation. Also, the number of parts can be reduced: Low voltage technology allows it to pack in one chip several 1×N multiplexers, with N being higher than in high voltage multiplexers. Preferred low-voltage multiplexers use CMOS technology.

In a preferred embodiment of the invention, the transmission side of the ultrasound system channels comprises a high-voltage multiplexer. Separation of transmission and reception channels can considerably reduce the requirements for the high-voltage multiplexer entailing lower cost. For example, switching time requirements are reduced as reception can start immediately after transmission with no delay necessary for recovering. Moreover, the high-voltage multiplexer needs not be suitable for dealing with low-voltage signals, as in the conventional system. As in the present embodiment, in contrast to the conventional technology, the transmission side and the reception side no longer share the same multiplexer, advantageously different transducer element combinations on the transmission side may be used than on the reception side. This allows for a simpler design of the transmission side which may for example result in considerably lower costs. The invention also comprises embodiments where there is no multiplexer present on the transmission side. For example, a multiplexer may not be needed on the transmission side if a single wide wave front that covers the whole width of the probe is generated by one or a few element(s), such that no scanning over the elements is necessary on the transmission side.

A preferred ultrasound system also comprises a Low Noise Amplifier (LNA), which can be placed upstream or downstream the multiplexer on the reception side. Preferably, the photo detector's output is fed directly into the LNA. This is in contrast to the conventional set up, where the output signal of the ultrasound sensor of the reception channel, which is also the transducer of the transmission channel, usually first passes a transmit/receive switch and a protection circuit to prevent saturation. According to the present invention, the transmit/receive switch is redundant and the function of the saturation protection can be performed by the intensity adjustment means. It is an achievable advantage of this embodiment of the invention, that noise and attenuation that would otherwise result from the transmit/receive switch and a protection circuit can be reduced. The output of the LNA is preferably passed through a cable to a multiplexer, preferably a low-voltage multiplexer.

In a preferred embodiment of the invention, the output of the LNA is fed directly into the low-voltage multiplexer, preferably doing away with the cable. Thereby, the ultrasound sensor can be integrated with the LNA and the low-voltage multiplexer in the probe head. This embodiment allows for a more compact and easier to handle system-in-a-probe device.

The preferred ultrasound system also comprises an Analog/Digital Converter (ADC), which converts the amplified output of the photo detector into digital signals. A preferred ADC is a Delta Sigma ADC, preferably a Continuous-Time Delta Sigma ADC (also often referred to as a Continuous-Time Sigma Delta ADC), with an improved signal-to-noise ratio as compared to the traditional pipeline ADC architecture, thereby improving the dynamic range. It is an achievable advantage of this latter embodiment of the invention, that a lower resolution Delta Sigma ADC, e.g. a 14-bit ADC, can be used instead of a higher resolution conventional ADC, e.g. a 16-bit ADC, thereby saving cost and power. The ADC preferably is located downstream the LNA e.g. after the low-voltage multiplexer. Furthermore, there is no aliasing in Delta Sigma ADC's compared to the traditional pipeline ADC architecture. It is an achievable advantage of this latter embodiment of the invention that using Delta Sigma ADC's removes the need for components performing anti aliasing filter compared to an architecture using traditional pipeline ADCs, thereby saving cost and power and space on PCBs.

In a preferred embodiment of the invention, the LNA's signal is fed directly into the Analog/Digital Converter. This may allow for integrating the ultrasound sensor with the LNA and the ADC in the probe head. This way, digital signals instead of analog signals can be sent to the processing unit, allowing for simpler and less costly cables. The integration may also lead to a considerable reduction in noise thereby improving image quality and reducing cost, size and/or power requirements. In this embodiment of the invention, preferably for each photo detector, which is preferably associated with one optical ultrasound detector, an individual LNA and ADC are provided forming an ultrasound detector/photo detector/LNA/ADC block. This way, advantageously the multiplexer can be made redundant or can be replaced by a digital multiplexer downstream the ADC. Alternatively, an analog multiplexer may be provided upstream of the LNA. In a particularly preferred embodiment of the invention, each photo detector of the opto-electrical ultrasound sensor is provided with its own LNA and ADC.

BRIEF DESCRIPTION OF THE DRAWINGS

The invention is illustrated in greater detail with the aid of schematic drawings.

FIG. 3 shows an embodiment of the invention where the Variable Gain Amplifier is omitted.

DETAILED DESCRIPTION OF THE EMBODIMENTS OF THE INVENTION

Figure 1:
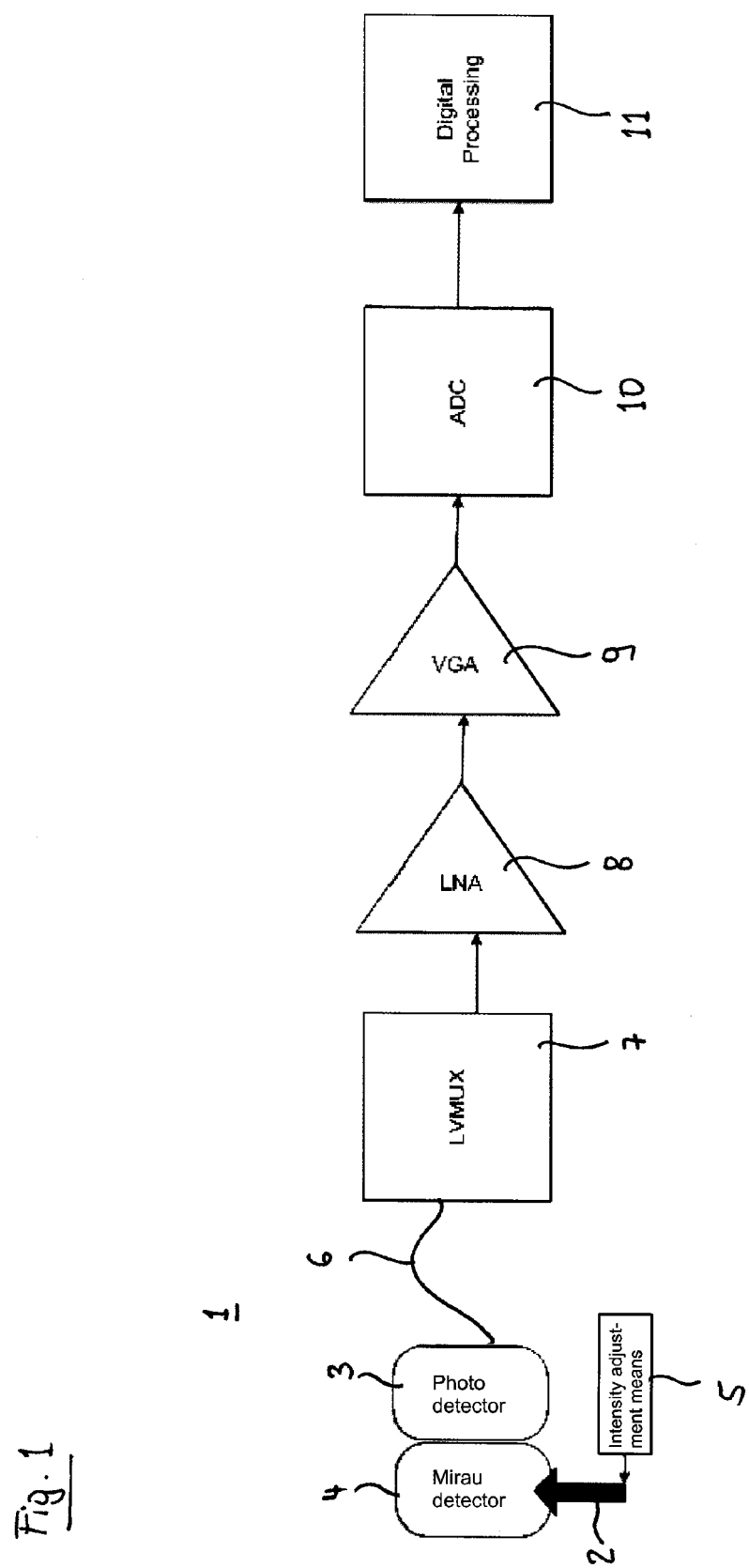
FIG. 1 shows a receive channel of a first embodiment of the invention where the electrical signals from the photo detector are passed via a cable through a low-voltage multiplexer, a Low-Noise Amplifier and a Variable Gain Amplifier to an Analog/Digital Converter.
Figure 2:
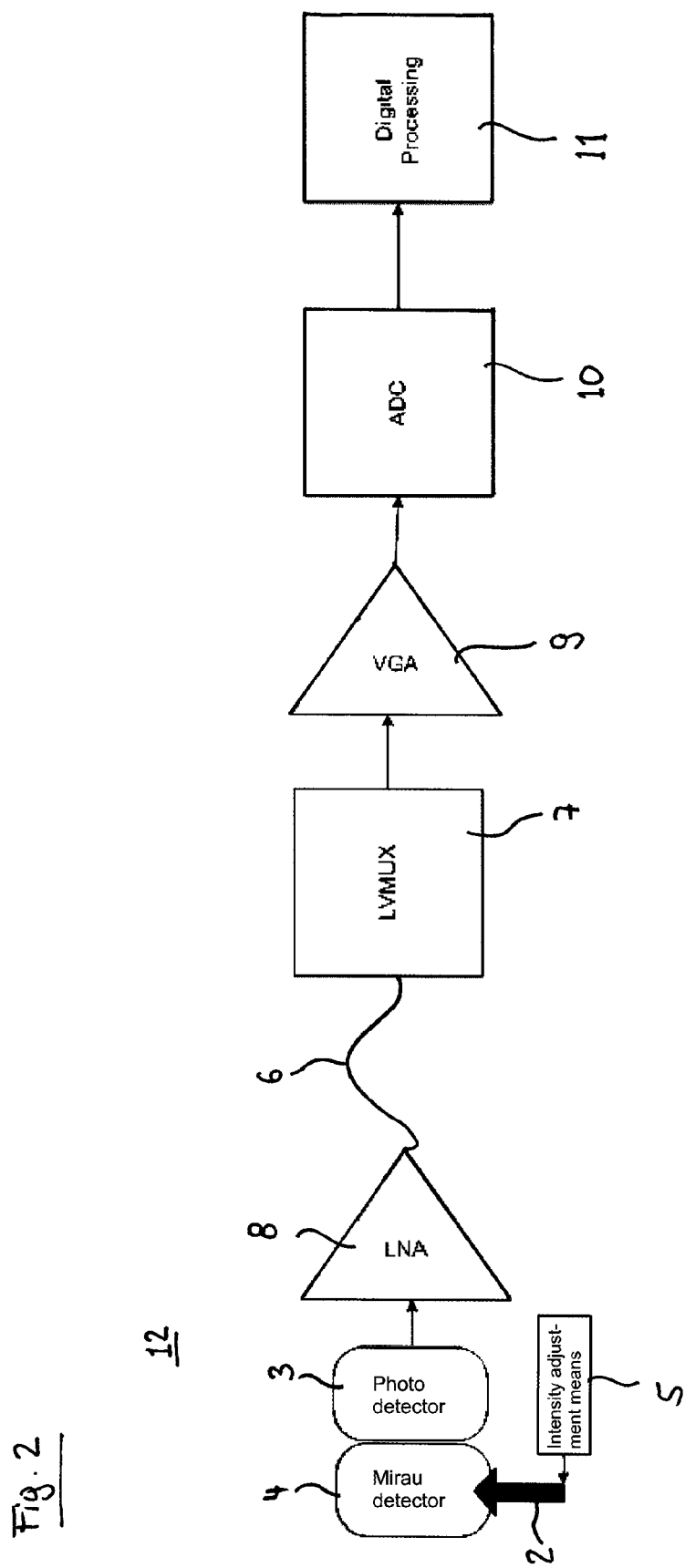
FIG. 2 shows another embodiment of the invention where the Low-Noise Amplifier is integrated with the corresponding photo detector into the probe head before the cable.

The FIGS. 1 to 3 show 3 different arrangements of receive channels of an ultrasound system according to the invention, in particular for the use in the medical diagnosis of a patient. In the reception channel 1 schematically shown in FIG. 1, a laser light source 2 illuminates a photo diode 3 as a photo detector, which is part of a photo diode array and produces electrical signals indicative of the intensity of the light incident on the photo diode. A Mirau optical ultrasound detector 4 as described in DE 10 2006 033 229 and which is part of a micro optical array of several Mirau optical ultrasound detectors, each associated with one photo diode of the photo diode array is placed in the optical path between the light source 2 and the photo diode 3, to modulate in response to an ultrasound signal the intensity of the light incident on the photo diode from the light source 2. The intensity of a light source 2 is adjusted by the intensity adjustment means 5 in order to match the signal picked up by the photo detector 3 to the photo detector's 3 dynamic range and that of the processing electronics upstream of the photo detector 3. For this purpose, the intensity adjustment means 5 is functionally connected with the photo diode 3.

The photo diode's 3 output signals are passed through a cable 6 to a low-voltage M×N multiplexer 7, where M is the number of receive channels (VCA and ADC) and N is the number of photo detectors in the array. The multiplexer's 7 output is further passed to a Low-Noise Amplifier (LNA) 8 and from there to a Variable Gain Amplifier (VGA) 9 which performs Time Gain Control (TGC) in order to compensating for the attenuation of the ultrasound signals that come from deeper regions of the tissue. The output from the VGA is sent to a Continuous-Time Delta Sigma Analog/Digital Converter (ADC) 10, which produces a digital signal that can be further processed in a digital processing unit 11, e.g. particular to form an image of the examined region.

The reception channel 12 in FIG. 2, differs from the one 1 in FIG. 1 in that the LNA 8 is now integrated with the photo detector 3 in the probe head before the cable 6. The photo diode's 3 output is fed directly into the LNA 8. Saturation protection is performed by the intensity adjustment means 5. The output of the LNA 8 is preferably passed through the cable 6 to the low-voltage multiplexer 7. In a variation (not shown) of this setup, the output of the LNA 8 is fed directly into the low-voltage multiplexer 7, doing away with the cable 6, and the low-voltage multiplexer is also integrated in the probe head. The multiplexer's 7 output is passed to the VGA 9 which performs TGC in order to compensating for the attenuation of the ultrasound signals that come from deeper regions of the tissue. The output from the VGA is sent to the ADC 10, which produces a digital signal that can be further processed in a digital processing unit 11.

FIG. 3 shows an example of a reception channel 13, where the VGA 9 is omitted. Instead, the Time Gain Control task is performed by the intensity adjustment means 5 by increasing from the moment in which a respective ultrasound signal has been emitted from an ultrasound transducer (not shown) the intensity linearly in dB. Moreover, as in the previous examples, the intensity adjustment means 5 also perform saturation protection. The photo diode's 3 output signals are fed directly into the LNA 8, which is integrated with the photo diode 3. From there, the signals are passed through a cable to the multiplexer 7 and from there to the ADC 10, which produces a digital signal that can be further processed in a digital processing unit 11. In a variation (not shown) of this setup, the output of the LNA 8 is fed directly into the ADC 10, doing away with the low-voltage multiplexer. With each photo detector 3, a corresponding LNA 8 and ADC 10 are integrated in the probe head.

The features described in the above description, claims and figures can be relevant to the invention in any combination.

The invention claimed is:

1. An opto-electrical ultrasound sensor for use in medical diagnostics comprising:
    at least one light source;
    at least one photo detector illuminated by the light source and capable of producing an electrical signal indicative of intensity of light incident on the photo detector; and
    at least one optical ultrasound detector located in an optical path between the light source and the photo detector and capable of modulating, in response to an ultrasound signal, the intensity of at least part of the light incident on the photo detector from the light source; and
    an intensity adjustment for adjusting the intensity of the light signal incident on the photo detector via the optical ultrasound detector; wherein
    the intensity adjustment is functionally connected to the photo detector and is adapted to adjust the intensity of the light as a predetermined function of time to perform a time gain control, thereby at least partially compensating for attenuation of the ultrasound signal as it emanates from increasingly greater depth in tissue being examined by said opto-electrical ultrasound sensor.

2. The opto-electrical ultrasound sensor according to claim 1, wherein the intensity adjustment is adapted to control the light source to adjust the intensity of the light emitted by the light source.

3. The opto-electrical ultrasound sensor according to claim 1, wherein the intensity adjustment comprises an attenuator located in the optical path from the light source to the photo detector via the optical ultrasound detector, said attenuator adapted to attenuate at least part of the light incident on the photo detector.

4. The opto-electrical ultrasound sensor according to claim 3, wherein the attenuator comprises a Pockels cell.

5. The opto-electrical ultrasound sensor of claim 1, wherein the intensity adjustment is adapted to reduce the intensity to prevent the electrical signal produced by the photo detector to exceed a pre-determined level.

6. The opto-electrical ultrasound sensor according to claim 1, wherein the intensity adjustment is adapted to adjust the intensity in response to the electrical signal produced by the photo detector.

7. An ultrasound system comprising:
   a transmission side having at least one transmission channel to generate an ultrasound signal; and
   a reception side having at least one reception channel to detect and process the ultrasound signal; wherein:
   the reception side comprises at least one opto-electrical ultrasound sensor according to claim 1.

8. The ultrasound system according to claim 7 wherein the transmission side comprises at least one ultrasound transducer to generate the ultrasound signal, the at least one ultrasound transducer being different from the opto-electrical ultrasound sensor of the reception side.

9. The ultrasound system according to claim 8, wherein the transducer comprises PVDF (Polyvinylidene Difluoride) as piezoelectric material.

10. The ultrasound system according to claim 7, wherein the reception side comprises at least one low-voltage multiplexer.

11. The ultrasound system according to claim 10, wherein the transmission side comprises at least one high-voltage multiplexer.

12. The ultrasound system according to claim 7, wherein the reception side comprises at least one low-noise amplifier.

13. The ultrasound system of claim 12, wherein an output of the photo detector is fed directly into an input of the low-noise amplifier.

14. The ultrasound system of claim 13, wherein each low-noise amplifier is associated with one optical ultrasound detector.

15. The ultrasound system according to claim 12, wherein an output of the low-noise amplifier is fed directly into a low-voltage multiplexer.

16. The ultrasound system according to claim 7, further comprising an analog/digital converter.

17. The ultrasound system of claim 16, wherein a signal emanating from a low-noise amplifier is fed directly into the analog/digital converter.

18. The ultrasound system according to claim 7, further comprising a plurality of analog/digital converters, wherein each analog/digital converter is associated with one low-noise amplifier.

19. A method for detecting ultrasound for use in medical procedures which comprises:
   illuminating a photo detector with a light source, the photo detector producing an electrical signal indicative of intensity of light incident on the photo detector;
   modulating, in response to an ultrasound signal, the intensity of at least part of the light incident on the photo detector from the light source by means of an optical ultrasound detector located in an optical path between the light source and the photo detector; and
   adjusting the intensity of the light signal incident on the photo detector via the optical ultrasound detector by an intensity adjustment; wherein
   the intensity of the light signal is adjusted by the intensity adjustment as a predetermined function of time to perform a time gain control, thereby at least partially compensating for attenuation of the ultrasound signal as it emanates from increasingly greater depth in tissue being examined.

* * * * *